US00PP23523P2

(12) United States Plant Patent
van Kleinwee

(10) Patent No.: US PP23,523 P2
(45) Date of Patent: Apr. 9, 2013

(54) ***BIDENS* PLANT NAMED 'BIDZ0002'**

(50) Latin Name: *Bidens ferulifolia*
Varietal Denomination: BIDZ0002

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 21 days.

(21) Appl. No.: 13/317,609

(22) Filed: Oct. 24, 2011

(51) Int. Cl.
*A01H 5/00* (2006.01)

(52) U.S. Cl. ..... Plt./410

(58) Field of Classification Search ..... Plt./410
See application file for complete search history.

*Primary Examiner* — Susan McCormick Ewoldt
(74) *Attorney, Agent, or Firm* — Joshua L. Price

(57) ABSTRACT

A new *Bidens* plant named 'BIDZ0002' particularly distinguished by the smaller, semi-double type, bright yellow inflorescences, with free branching and good floriferousness, relatively compact, mounded and denser plant habit.

1 Drawing Sheet

Latin name of the genus and species of the plant claimed: *Bidens ferulifolia*.

Varietal denomination: 'BIDZ0002'.

BACKGROUND OF THE NEW PLANT

The present invention comprises a new *Bidens* plant, botanically known as *Bidens ferulifolia* and hereinafter referred to by the variety name 'BIDZ0002'.

'BIDZ0002' is a product of a planned breeding program. The new cultivar has smaller, semi-double type, bright yellow inflorescences, with free branching and good floriferousness, relatively compact, mounded and denser plant habit.

'BIDZ0002' originates from open pollination made in the summer of 2006 in a controlled breeding program in the trial field in Enkhuizen, Netherlands. The female parent was a proprietary plant designated 'F0020-1', having larger, single-type, yellow colored flowers and stronger growth habit.

The male parent of 'BIDZ0002' is an unknown plant. The resultant seeds were sown in March 2007.

'BIDZ0002' was selected as one flowering plant within the progeny of the stated cross in May 2007 in a controlled environment in Enkhuizen, Netherlands.

The first act of asexual reproduction of 'BIDZ0002' was accomplished when vegetative cuttings were propagated from the initial selection in the early summer of 2007 in a controlled environment in Enkhuizen, Netherlands.

BRIEF SUMMARY OF INVENTION

Horticultural examination of plants grown from cuttings of the plant initiated in February 2008 in Enkhuizen, Netherlands, and continuing thereafter, has demonstrated that the combination of characteristics as herein disclosed for 'BIDZ0002' are firmly fixed and are retained through successive generations of asexual reproduction.

'BIDZ0002' has not been observed under all possible environmental conditions. The phenotype may vary significantly with variations in environment such as temperature, light intensity and day length.

Plant Breeder's Rights for this cultivar were applied for in Canada on Dec. 24, 2010, #10-71350 and with the CPVO on Oct. 15, 2010, #2010/2181. 'BIDZ0002' has not been made publicly available more than one year prior to the filing of this application.

The following traits have been repeatedly observed and are determined to be basic characteristics of the new variety. The combination of these characteristics distinguishes this *Bidens* as a new and distinct variety.

BRIEF DESCRIPTION OF THE PHOTOGRAPHS

Figure 1:
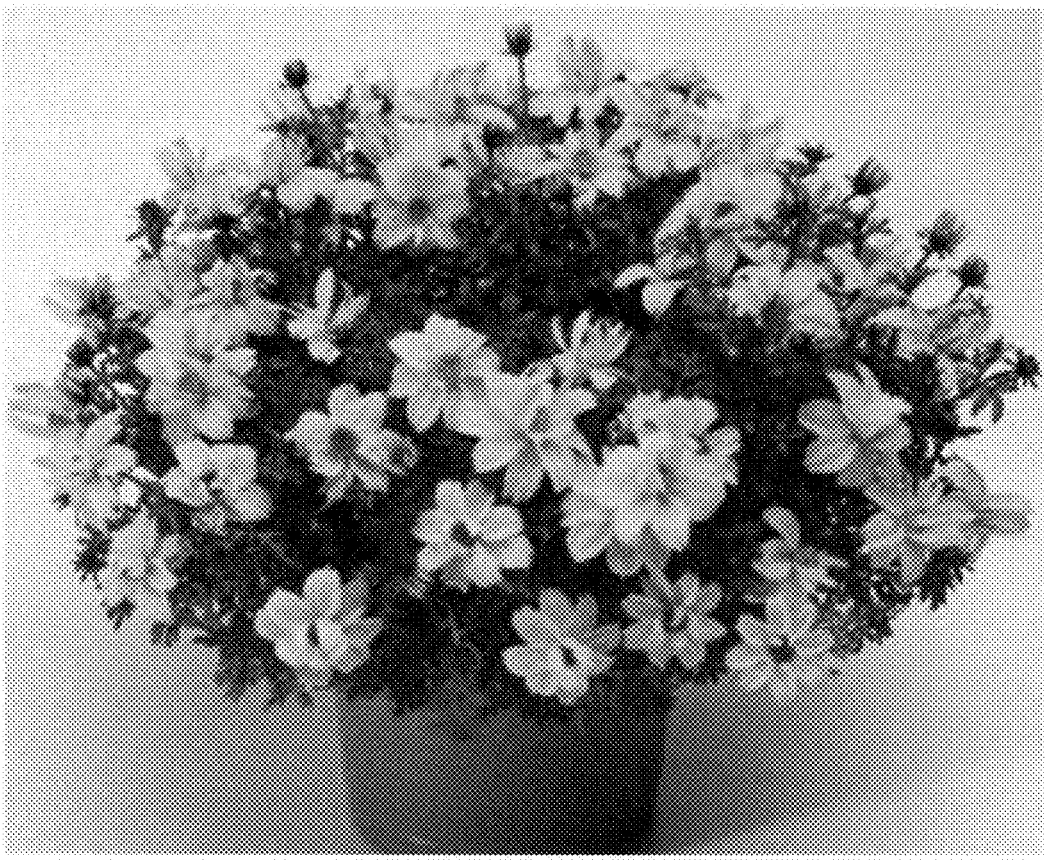
Figure 2:
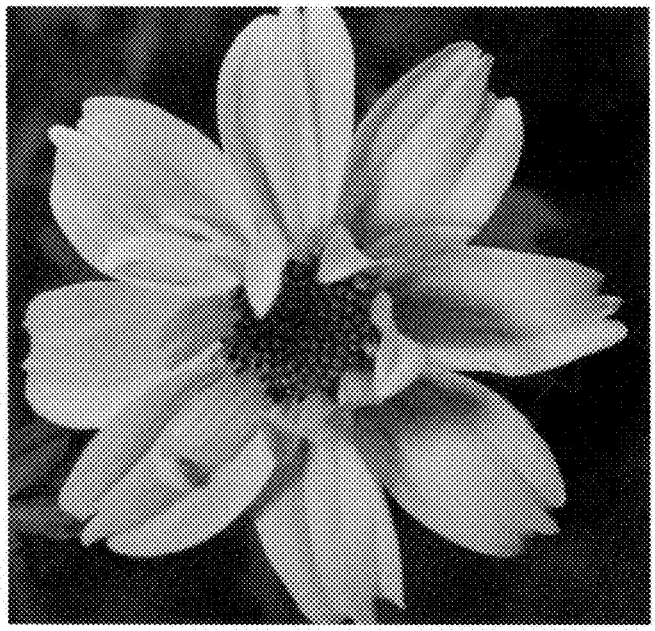

The accompanying photographic drawing shows typical flower and foliage characteristics of 'BIDZ0002' with colors being as true as possible with an illustration of this type. The photographic drawing shows in FIG. 1. a flowering plant of the new variety and in FIG. 2. a close-up of the flowers.

DETAILED BOTANICAL DESCRIPTION

The aforementioned photographs were taken in mid June 2010 from plants grown in a greenhouse trial in Enkhuizen, Netherlands. These plants were growing in 12 cm pots and were approximately 14-15 weeks of age.

The plant descriptions and measurements were taken in mid May 2011 in Andijk, Netherlands on about 12 week old plants. These plants were growing on benches in a greenhouse at moderately warm conditions (14/16° C.).

Color references are made to The Royal Horticultural Society Colour Chart (R.H.S.) 2001.

TABLE 1

DIFFERENCES BETWEEN THE NEW VARIETY 'BIDZ0002' AND A SIMILAR VARIETY

| | 'BIDZ0002' | Pirate's Treasure (Unpatented) |
|---|---|---|
| Inflorescence, diameter: | 3.6-4.3 cm | 2.9-3.0 cm |
| Flower color: | Deep yellow, RHS 9A | More golden yellow, RHS 12A with shades of 13A |
| Stem length: | 17-23 cm | Up to 30 cm |

Plant:
*Form, growth and habit.*—Herbaceous, cultivated as an annual plant, free branching, relatively compact, mounded and dense.
*Plant height.*—11.0-17.0 cm.
*Plant height (inflorescence included).*—18.0-23.0 cm.
*Plant width.*—40.0 cm.
Roots:
*Number of days to initiate roots and develop roots.*—21-24 days at about 22 degrees C.
*Type.*—Fine, fibrous, free branching.
*Color.*—RHS N155B but whiter.
Foliage:
*Arrangement.*—Opposite, decussate.
*Immature leaf, color upper surface.*—RHS 137C to RHS 137D.
*Immature leaf, color lower surface.*—RHS 138B.
*Mature leaf, color upper surface.*—RHS 137A to RHS 137B.
*Mature leaf, color lower surface.*—RHS 138B.
*Length.*—2.4-2.6 cm.
*Width.*—2.0-2.2 cm.
*Shape.*—Roughly deltoid, bi-pinnate.
*Base shape.*—Nearly truncate.
*Apex shape.*—Acute.
*Margin.*—Deeply incised.
*Texture upper surface.*—Smooth, glabrous, somewhat glossy.
*Texture lower surface.*—Sparse hair, mainly along the veins.
*Vein color, upper surface.*—About RHS 138B but almost indistinct.
*Vein color, lower surface.*—RHS 144A.
Petiole:
*Petiole color, upper side.*—RHS 137D.
*Petiole color, lower side.*—RHS 145A.
*Petiole length.*—0.3-0.5 cm.
*Diameter of petiole.*—0.15 cm.
*Texture.*—Smooth, hirsute mainly along the margins.
Stems:
*Quantity of main branches per plant.*—About 23-27.
*Color of stem.*—RHS 144B; partly with a little anthocyanin of RHS 165A.
*Length of stem.*—17.0-23.0 cm.
*Stem diameter.*—0.2-0.3 cm.
*Length of internodes.*—2.0-4.0 cm.
*Texture.*—Fine pubescence.
Peduncle:
*Color.*—RHS 145A.
*Length of peduncle.*—3.0-6.0 cm.
*Diameter.*—1.0-1.5 cm.
*Texture.*—Slightly furrowed near the flower base, very fine pubescence.
Inflorescence:
*Type.*—Solitary inflorescences, terminal, composite type inflorescences positioned above the foliage; inflorescences face upright.
*Blooming habit.*—Continuous flowering from spring through fall.
*Quantity of inflorescences per plant.*—About 20-40.
*Lastingness of inflorescences.*—Approximately 7-8 days, depending on temperature.
*Fragrance.*—None.
Bud:
*Color.*—RHS 7B.
*Length.*—0.7-1.1 cm.
*Width.*—0.7 cm.
*Shape.*—Ovoid.
Mature inflorescence:
*Inflorescence horizontal diameter.*—3.6-4.4 cm.
*Inflorescence depth.*—2.6 cm.
*Disc diameter.*—0.7 cm.
Ray florets:
*Number of ray florets per inflorescence.*—Usually 7-8, with extra petaloids.
*Color of upper surface.*—RHS 9A.
*Color of lower surface.*—RHS 9B.
*Length.*—1.6-1.9 cm.
*Width.*—0.8-1.1 cm.
*Shape.*—Elliptical.
*Apex.*—Obtuse to slightly dentate or praemorse.
Petaloids:
*Quantity of petaloids.*—1-2 per floret, 8-16 per inflorescense.
*Color of upper surface.*—RHS 9A.
*Color of lower surface.*—RHS 9B.
*Length of upright rays.*—1.1-1.4 cm.
*Width.*—0.3-0.4 cm.
*Shape.*—Ensiform.
*Apex.*—Acute.
All petals:
*Base.*—Fused.
*Margins.*—Entire.
*Texture.*—Smooth and glabrous on both surfaces.
Disc florets:
*Number of disc florets per inflorescence.*—About 40-50 initially; (quantity is known to lessen as the plants get older, about 25-30).
*Color of immature disc florets.*—RHS 177A.
*Color of mature disc florets.*—RHS 5B, fading towards base.
*Mature, length.*—0.4 cm.
*Mature, width at apex.*—0.1-0.15 cm.
*Shape.*—Tubular.
Receptaculum:
*Diameter.*—0.6-0.8 cm.
*Depth.*—0.4 cm.
*Shape.*—Semi-spherical.
*Number of phyllaries.*—Approximately 16-18.
*Phyllary color.*—RHS 137A, upmost phyllaries have semi-transparent margins.
*Phyllary length.*—0.4 cm.
*Phyllary width.*—0.15 cm.
*Phyllary shape.*—Ensiform to oblanceolate.
*Phyllary shape of apex.*—Obtuse or broadly acute.
*Phyallary base.*—Attenuate.
*Phyllary margin.*—Entire.
*Phyllary texture of upper surface.*—Glossy, glabrous.
*Phyllary texture of lower surface.*—Sparse, very short hairs.
Reproductive organs:
*Gynoecium.*—Pistil: One. Length: 0.7 cm. Style length: 0.3-0.4 cm. Stigma shape: Cleft, reflexed. Stigma color: RHS 13C.
*Androecium.*—Number of anthers: One androecium, tube-shaped, formed by fused stamen. Length of anthers: 0.4 cm. Anther color: RHS 200A. Pollen amount: Moderate. Color of pollen: RHS 12A.
Fertility/seed set: Fertility/seed set has not been observed on this hybrid.
Disease/pest resistance: Diesease/pest resistance has not been observed on this hybrid.

What is claimed is:

1. A new and distinct variety of *Bidens* plant named 'BIDZ0002' substantially as illustrated and described herein.

* * * * *